(12) United States Patent
Abrams et al.

(10) Patent No.: US 8,128,614 B2
(45) Date of Patent: Mar. 6, 2012

(54) MODULAR STEERABLE SHEATH CATHETERS

(75) Inventors: Robert M. Abrams, Los Gatos, CA (US); Michael P. Wallace, Pleasanton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 229 days.

(21) Appl. No.: 12/353,112

(22) Filed: Jan. 13, 2009

(65) Prior Publication Data
US 2009/0124978 A1  May 14, 2009

Related U.S. Application Data

(63) Continuation of application No. 10/733,922, filed on Dec. 10, 2003, now Pat. No. 7,481,793.

(51) Int. Cl.
*A61M 25/01* (2006.01)
(52) U.S. Cl. .............. 604/528; 604/164.01; 604/536
(58) Field of Classification Search .............. 604/523, 604/525, 528, 533, 95.04, 164.01, 536
See application file for complete search history.

(56) References Cited

U.S. PATENT DOCUMENTS

| | | | |
|---|---|---|---|
| 4,582,181 A | 4/1986 | Samson | |
| 4,898,577 A * | 2/1990 | Badger et al. | 604/528 |
| 4,917,104 A | 4/1990 | Rebell | |
| 5,074,849 A | 12/1991 | Sachse | |
| 5,178,608 A | 1/1993 | Winters | |
| 5,226,427 A | 7/1993 | Buckberg et al. | |
| 5,263,493 A | 11/1993 | Avitall | |
| 5,312,360 A | 5/1994 | Behl | |
| 5,327,889 A | 7/1994 | Imran | |
| 5,391,155 A | 2/1995 | Sachse | |
| 5,407,435 A | 4/1995 | Sachse | |
| 5,425,709 A | 6/1995 | Gambale | |
| 5,439,445 A | 8/1995 | Kontos | |
| 5,471,982 A | 12/1995 | Edwards et al. | |
| 5,487,757 A * | 1/1996 | Truckai et al. | 604/264 |
| 5,497,782 A | 3/1996 | Fugoso | |
| 5,498,239 A * | 3/1996 | Galel et al. | 604/95.02 |
| 5,599,305 A | 2/1997 | Hermann et al. | |
| 5,843,031 A | 12/1998 | Hermann et al. | |
| 5,861,024 A | 1/1999 | Rashidi | |
| 5,935,098 A | 8/1999 | Blaisdell et al. | |
| 5,993,424 A | 11/1999 | Lorenzo et al. | |
| 6,066,125 A | 5/2000 | Webster, Jr. | |
| 6,117,140 A | 9/2000 | Munsinger | |
| 6,146,415 A | 11/2000 | Fitz | |
| 6,238,402 B1 | 5/2001 | Sullivan, III et al. | |

(Continued)

FOREIGN PATENT DOCUMENTS
EP  0565996 A1  10/1993

*Primary Examiner* — Laura Bouchelle
(74) *Attorney, Agent, or Firm* — Seager, Tufte & Wickhem, LLC (57) ABSTRACT

An apparatus for accessing a site within a body includes a cannula and an elongate member. The cannula has a proximal end, a distal end, and a lumen extending therebetween. The elongate member has a distal end configured for insertion into the lumen, wherein the distal end of the elongate member is attachable to and releasable from the distal end of the cannula. A method for accessing a site within a body includes inserting a distal end of an elongate member into a lumen of a cannula, detachably attaching the distal end of the elongate member to the cannula, and steering a distal end of the cannula to a desired site using the elongate member.

2 Claims, 7 Drawing Sheets

U.S. PATENT DOCUMENTS

| | | |
|---|---|---|
| 6,287,301 B1 | 9/2001 | Thompson et al. |
| 6,338,725 B1 | 1/2002 | Hermann et al. |
| 6,500,167 B1 | 12/2002 | Webster, Jr. |
| 6,514,261 B1 | 2/2003 | Randall et al. |
| 2001/0044624 A1 | 11/2001 | Seraj et al. |
| 2002/0133111 A1 | 9/2002 | Shadduck |
| 2003/0069522 A1 | 4/2003 | Jacobsen et al. |
| 2003/0109778 A1 | 6/2003 | Rashidi |
| 2003/0144657 A1 | 7/2003 | Bowe et al. |

* cited by examiner

Section A-A

MODULAR STEERABLE SHEATH CATHETERS

RELATED APPLICATION DATA

This application is a continuation application of co-pending U.S. patent application Ser. No. 10/733,922, filed Dec. 10, 2003, the priority of which is claimed under 35 U.S.C. §120, and the contents of which are incorporated herein by reference in their entirety, as though set forth in full.

FIELD OF THE INVENTION

The present invention relates generally to catheters, and more particularly to catheters that are used to provide access into a body for delivery of additional tools, instruments, medications, or fluids.

BACKGROUND

Catheters have been used to reach locations within a body otherwise unreachable without invasive surgery. A catheter has a distal end which is configured to enter a patient, such as a major vein, artery, or other body cavity. Once the tip of the catheter is inserted into the patient, the catheter is distally advanced until the distal end of the catheter reaches a target site.

Steerable mechanisms have been developed to facilitate the transit of catheters through a patient's blood vessels. In practice, a surgeon typically observes the catheter fluoroscopically and maneuvers the catheter by selective rotation and deflection of a steering mechanism of the proximal end of the catheter. The rotation and deflection at the proximal end bends or deflects the tip of the catheter and enables the surgeon to steer the catheter as it advances through the tortious path often found during the transit through a patient's blood vessels.

In many applications, the ability to steer the catheter is crucial to the success of a procedure and can be a factor in reducing risk to and trauma of the patient. Moreover, the ability to steer the catheter impacts the speed and ease by which the surgeon can properly position the distal end, particularly during heart mapping protocols.

The distal ends of some steerable catheters are formed of a shape memory material or structure, such as a coil spring, so that the application of a force to a steering cable (that is fixedly secured to a distal end of the catheter) deflects the distal tip of the catheter from its normal position. As the tension in the cable is released, the distal end tends to return to its normal position. The inclusion of the coil spring, cable, and other components of a steering mechanism at the distal end of the catheter imposes a limitation as to the smallest cross sectional dimension that the catheter can have. In addition, for catheters that have one or more working channels (e.g., for delivering fluids or tools), it may be difficult to secure the cable or other components of the steering mechanism to the distal end of the catheter in a way that does not interfere operations of the catheter.

Accordingly, improved devices and methods for providing access within a body would be useful.

SUMMARY OF THE INVENTION

In accordance with an embodiment of the invention, an apparatus for accessing a site within a body includes a cannula and an elongate member. The cannula has a proximal end, a distal end, and a lumen extending therebetween. The elongate member has a distal end configured for insertion into the lumen, wherein the distal end of the elongate member is attachable to and releasable from the distal end of the cannula. In one embodiment, the elongate member is a part of a steering device that is configured to steer the distal end of the cannula. In another embodiment, the elongate member is a stiffening element configured to increase a stiffness of the cannula.

In accordance with another embodiment of the invention, a method for accessing a site within a body includes inserting a distal end of an elongate member into a lumen of a cannula, detachably attaching the distal end of the elongate member to the cannula, and steering a distal end of the cannula to a desired site using the elongate member.

In accordance with another embodiment of the invention, a method for accessing a site within a body includes inserting a distal end of a first elongate member into a first lumen of a cannula to thereby increase a stiffness of the cannula, detachably attaching the distal end of the first elongate member to the cannula, and manipulating a proximal end of the cannula to thereby place a distal end of the cannula at a desired position.

In accordance with another embodiment, a method for accessing a site within a body includes inserting a wire having a bent configuration into a lumen of a cannula, the cannula having a distal end, a first portion at the distal end, and a second portion proximal to the first portion, wherein the second portion is relatively stiffer than the first portion, and manipulating the wire by sliding a distal end of the wire either distally or proximally relative to the cannula to thereby steer the distal end of the cannula.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting its scope, the invention will be described and explained with additional specificity and detail through the use of the accompanying drawings.

DETAILED DESCRIPTION OF THE ILLUSTRATED EMBODIMENTS

Various embodiments of the present invention are described hereinafter with reference to the figures. It should be noted that the figures are not drawn to scale and that elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an illustrated embodiment needs not have all the aspects or advantages of the invention shown. An aspect or an advantage described in conjunction with a particular embodiment of the present invention is not necessarily limited to that embodiment and can be practiced in any other embodiments of the present invention even if not so illustrated.

Figure 1A:
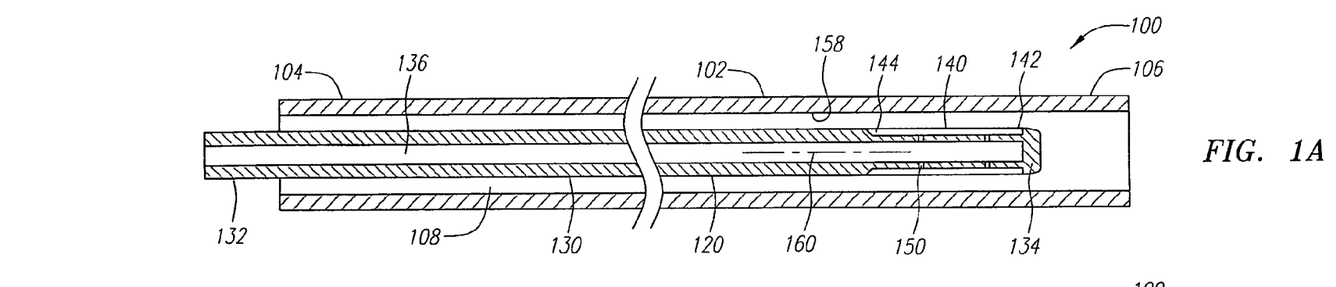
FIG. 1A illustrates a catheter for providing access into a body in accordance with an embodiment of the invention, which includes a cannula and a steering device having an expandable member.
Figure 1B:
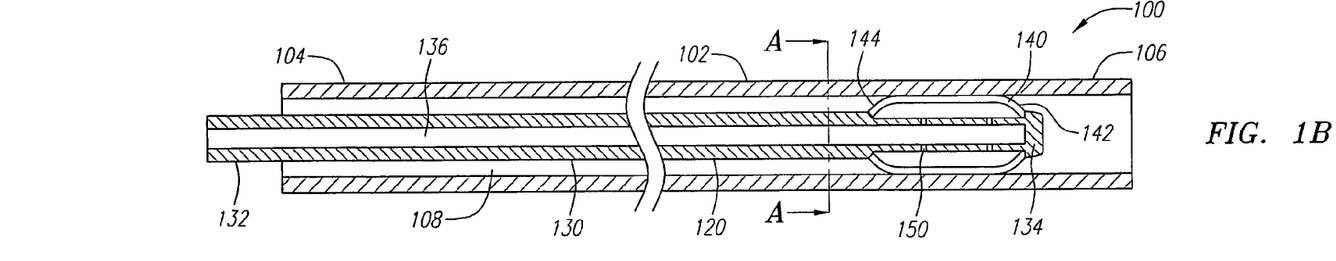
FIG. 1B illustrates the catheter of FIG. 1A, showing the expandable member being inflated.

FIGS. 1A and 1B illustrate a catheter 100 in accordance with an embodiment of the invention. The catheter 100 includes a cannula 102 and a steering device 120 that can be detachably secured to the cannula 102.

The cannula 102 has a proximal end 104, a distal end 106, and a lumen 108 extending between the proximal and distal ends 104, 106. In the illustrated embodiment, the distal end 106 has a cross sectional dimension that is between 0.7 mm and 1.2 mm, and more preferably between 0.9 mm and 1.0 mm. However, the distal end 106 of the cannula 102 may have other dimensions, depending on a particular application. The distal end 106 of the cannula can also has a tapered profile to allow ease of insertion into a site, such as a vein, an artery, an incision, a burr, and a breast duct. The cannula 102 can further include a radiopaque marker (not shown) secured to the distal end 106 of the cannula 102, or alternatively, a marker located at an exterior surface of the cannula 102, to assist a placement of the distal end 106 of the cannula 102 during use.

The cannula 102 can be made from a variety of materials, such as, a metal, an alloy, or a polymeric, electrically non-conductive material, like polyethylene, polyurethane, or PEBAX® material (polyurethane and nylon). Even more alternatively, the distal end 106 is made softer than the proximal portion of the cannula 102 by using different material and/or having a thinner wall thickness. This has the benefit of reducing the risk of injury to tissue that the distal end 106 may come in contact with during an operation. In another embodiment, the cannula 102 can also include a liner secured to an interior wall 158 of the cannula 102, the liner being composed of a suitable low friction material, e.g., TEFLON®, Poly-etheretherketone (PEEK), polyimide, nylon, polyethylene, or other lubricious polymer linings, to reduce surface friction with a device as the device slides within the lumen 108. In some embodiments, the cannula can be made torsionally stiff enough such that 1 degree of rotation at a proximal end creates a substantially 1 degree of rotation at the distal end. Also, in other embodiments, the cannula 102 can further include one or more openings or slots at the wall of the cannula 102 to provide a desired flexural and/or torsional stiffness to the cannula 102. The openings or slots can extend partially or completely through a thickness of the wall of the cannula 102.

The steering device 120 is configured to removably secure to the distal end 106 of the cannula 102, and can be used to steer the distal end 106 of the cannula 102 after the steering device 120 is secured to the cannula 102. As shown in the illustrated embodiment, the steering device 120 includes a shaft 130 having a proximal end 132, a distal end 134, and a lumen 136 extending therebetween, and an expandable member 140 secured to the distal end 134. In another embodiment, the steering device 120 can further include a handle connected to the proximal end 132 for adjusting or applying a tension force to the shaft 130. Any of the materials described previously with reference to the cannula 102 is also suitable for construction of the shaft 130. In some embodiments, the shaft 130 can be made torsionally stiff enough such that 1 degree of rotation at a proximal end creates a substantially 1 degree of rotation at the distal end. Also, in some embodiments, the shaft 130 can further include one or more openings or slots at the wall of the shaft 130 to provide a desired flexural and/or torsional stiffness to the shaft 130. In the illustrated embodiment, the expandable member 140 is made from a polymer. However, the expandable member 140 can also be made from other elastic materials. The expandable member 140 has a distal end 142 that is secured to the distal end 134 of the shaft 130, and a proximal end 144 that is secured to the shaft 130 at a point that is proximal to the distal end 134. Such configuration provides axial stiffness to the steering device 120 where the expandable member 140 is located, and prevents the expandable member 140 from buckling or collapsing as the distal end 134 of the shaft 130 is advanced distally within the lumen 108. Alternatively, the expandable member 140 can be constructed to have sufficient axial strength, and the proximal end 144 of the expandable member 140 can be secured to the distal end 134 of the shaft 130.

As shown in FIG. 1A, the expandable member 140 has a low profile and forming a substantially continuous surface with the shaft 130 when in a collapsed configuration. The low profile of the expandable member 140 allows ease of insertion and advancement within the lumen 108 of the cannula 102. During use, the expandable member 140 is advanced distally within the lumen 108 of the cannula 102 until the expandable member 140 reaches the distal end 106 of the cannula 102 (or until the expandable member 140 is desirably placed). Inflation fluid, such as saline or gas is then delivered via the lumen 136 of the shaft 130, and exits from one or more openings 150 located on the shaft 130 to inflate the expandable member 140 (FIG. 1B). The expandable member 140 is inflated until the expandable member 140 exerts a force against an interior surface of the cannula 102 sufficient to prevent relative movement between the distal end 134 of the shaft 130 and the distal end 106 of the cannula 106 during use of the steering device 120. After the distal end 134 of the shaft 130 has been secured to the cannula 102, the cannula 102 is then inserted into a body, and the proximal end 132 of the shaft 130 can be manipulated to change a shape of the distal end 106 of the cannula 102 to thereby steer the distal end 106. Particularly, pulling the proximal end 132 of the shaft 130 proximally will apply tension to the shaft 130, thereby causing the distal end 106 of the cannula 102 to bend, and releasing the tension in the shaft 130 will cause the distal end 106 of the cannula 102 to return to its original shape.

After the distal end 106 of the cannula 102 has been steered to a desired site within a body, the expandable member 140 is then deflated, and the steering device 120 can be removed from the lumen 108 of the cannula 102. The lumen 108 can then be used to deliver a tool, an instrument, a therapeutic element (such as a vaso-occlusive device, a stent, or a radiation seed), a diagnostic element, or a fluid.

Figure 1C:
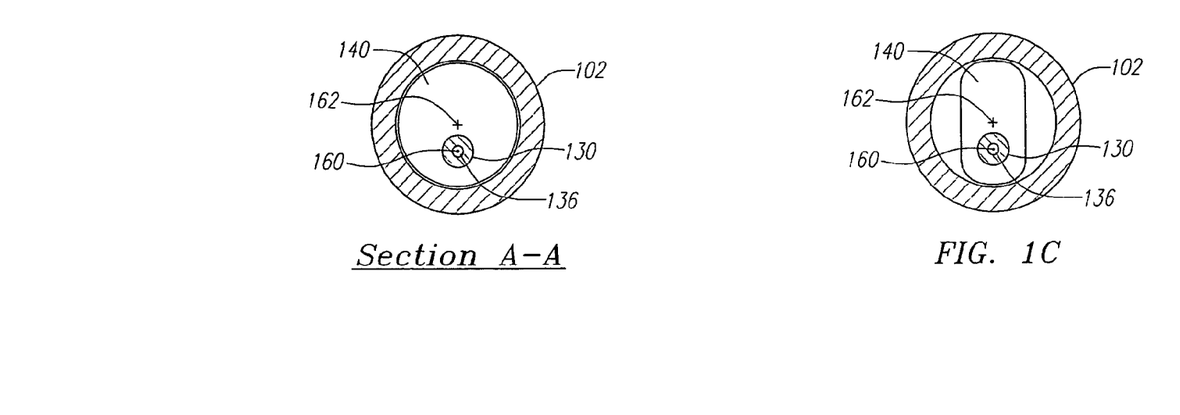
FIG. 1C illustrates a variation of a cross section of the catheter of FIG. 1A, showing the expandable member having an elliptical cross sectional shape.

In the illustrated embodiment, inflation of the expandable member 140 causes an axis 160 of the shaft 130 to offset from a center 162 of the cannula 102 at an axial position where the expandable member 140 is located. This can be accomplished by making a wall of a portion of the expandable member 140 relatively thicker than an adjacent portion. As the expandable member 140 is inflated, the thinner portion of the expandable member 140 will expand or stretch relatively more than the thicker portion of the expandable member 140. Such configuration provides a biased direction of a bending of the distal end 106, thereby allowing a physician to determine a direction in which the distal end 106 of the cannula 102 will bend upon pulling of the shaft 130. In the illustrated embodiment, the expandable member 140 substantially occupies the lumen 108 at a cross section of the cannula 102. Alternatively, the expandable member 140 can have other cross sectional shape, such that an elliptical shape (FIG. 1C), after it is inflated, such that the expandable member 140 does not completely occupies the lumen 108 at a cross section of the cannula 102. Such configuration allows the cannula 102 to deliver fluid or a tool even after the distal end 134 of the shaft 130 has been secured to the cannula 102.

Figure 2:
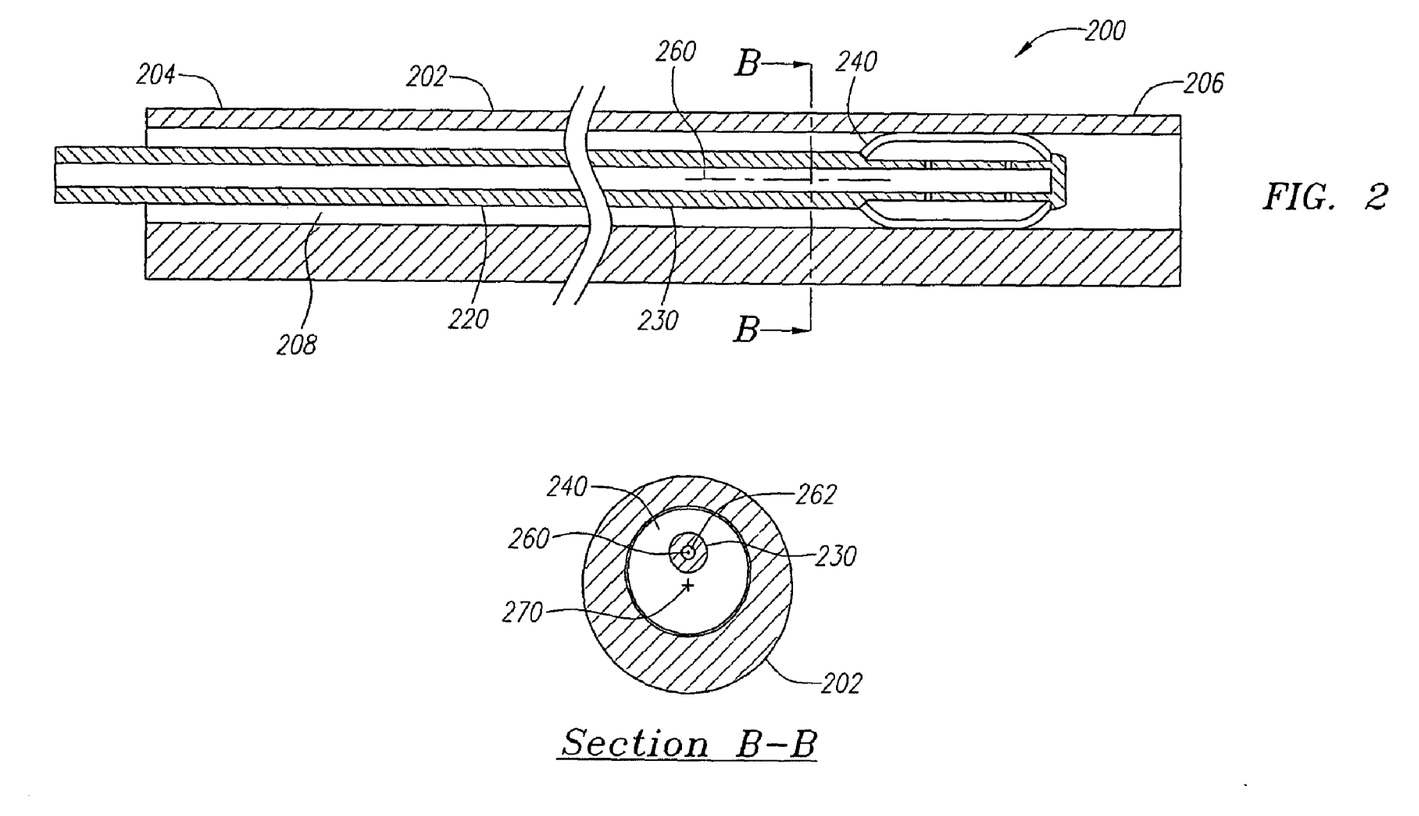
FIG. 2 illustrates a variation of the catheter of FIG. 1, particularly showing a lumen of a cannula that is off-center.

FIG. 2 shows another catheter 200 in accordance with an embodiment of the invention. The catheter 200 includes a cannula 202 having a proximal end 204, a distal end 206, and a lumen 208 extending therebetween. The catheter 200 also includes a steering device 220 having an expandable member 240. The cannula 202 and the steering device 220 are similar to the cannula 102 and the steering device 120 discussed previously, except that the lumen 208 of the cannula 102 is offset from a center 270 of the cannula 202. In such case, the expandable member 240 is configured to expand uniformly radially at a cross section such that an axis 260 of a shaft 230 of the steering device 220 is not substantially offset from a center 262 of the expandable member 240. The offset of the lumen 208 from the center 270 of the cannula 202 provides a biased direction of a bending of the distal end 202. Alternatively, the expandable member 240 can have a configuration that is similar to that of FIG. 1B, such that the axis 260 of the shaft 230 can be further offset from the center 270 of the cannula 202 after inflation of the expandable member 240.

Figure 3A:
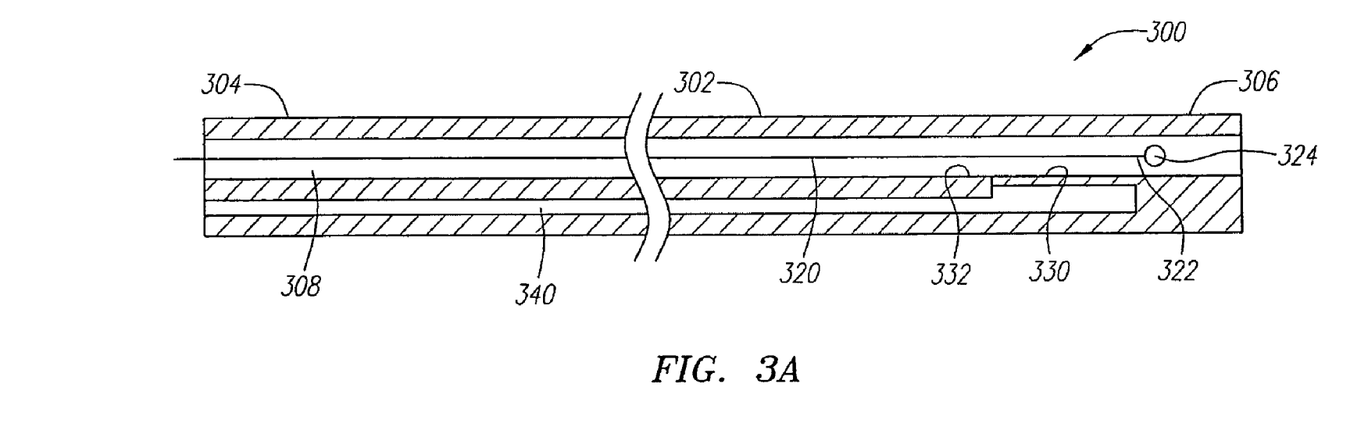
FIG. 3A illustrates a catheter for providing access into a body in accordance with another embodiment of the invention, which includes a cannula having an interior wall that can be expended radially inward.
Figure 3B:
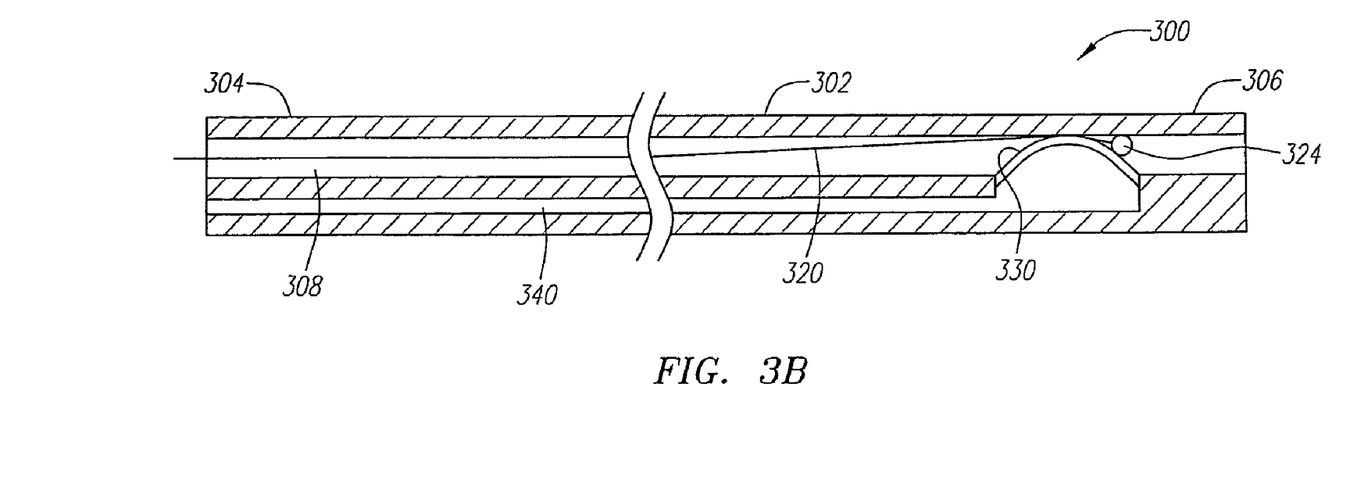
FIG. 3B illustrates the catheter of FIG. 3A, showing the interior wall of the cannula compressing against a wire.

It should be noted that the manner in which the steering device is secured to the cannula is not necessarily limited to the embodiments discussed previously, and that a variety of securing mechanisms can be employed. FIGS. 3A and 3B illustrate a catheter 300 in accordance with another embodiment of the invention. The catheter 300 includes a cannula 302 and a wire 320. The cannula 302 has a proximal end 304, a distal end 306, and a lumen 308 extending therebetween. The cannula 302 also includes an expandable member 330 and an inflation lumen 340 for delivering fluid to inflate the expandable member 330. In the illustrated embodiment, the expandable member 330 is constructed as a portion of a wall 332 of the cannula 302 that is relatively thinner than an adjacent portion of the wall 332. Alternatively, the expandable member 330 can be a membrane that covers and seals an opening at the wall 332 of the cannula 302. The membrane can be made of a polymer or other elastic materials.

During use, the wire 320 is inserted into the lumen 308 of the cannula 302 and is advanced distally until a distal end 322 of the wire 320 reaches the distal end 306 of the cannula 302. Inflation fluid is then delivered via the lumen 340 to cause the expandable member 330 to expand radially inwardly within the lumen 308. The expandable member 330 is expanded until it compresses the wire 320 against an interior wall of the cannula 302 with a force sufficient to prevent the wire 320 from moving relative to the distal end 306 (FIG. 3B). In the illustrated embodiment, the wire 320 includes an anchor member 324 in a form of a sphere that is secured to the distal end 322. The anchor member 324 is configured to provide additional anchorage of the wire 320 against the inflated expandable member 330 during use. Alternatively, the anchor member 324 can have other shapes or configurations. For example, in another embodiment, the anchor member 324 can be formed by bending the distal end 322 of the wire 320.

After the wire 320 has been secured to the cannula 302, the cannula 302 is then inserted into a body, and the wire 320 can be manipulated to steer the distal end 306 of the cannula 302 until the distal end 306 reaches a desired site. The expandable member 330 is then deflated to its unexpanded configuration to release the wire 320. After the wire 320 is removed from the lumen 308 of the cannula 302, the lumen 308 can be used to deliver a tool, an instrument, a therapeutic element (such as a vaso-occlusive device, a stent, or a radiation seed), a diagnostic element, or fluid, as similarly discussed previously.

Figure 4A:
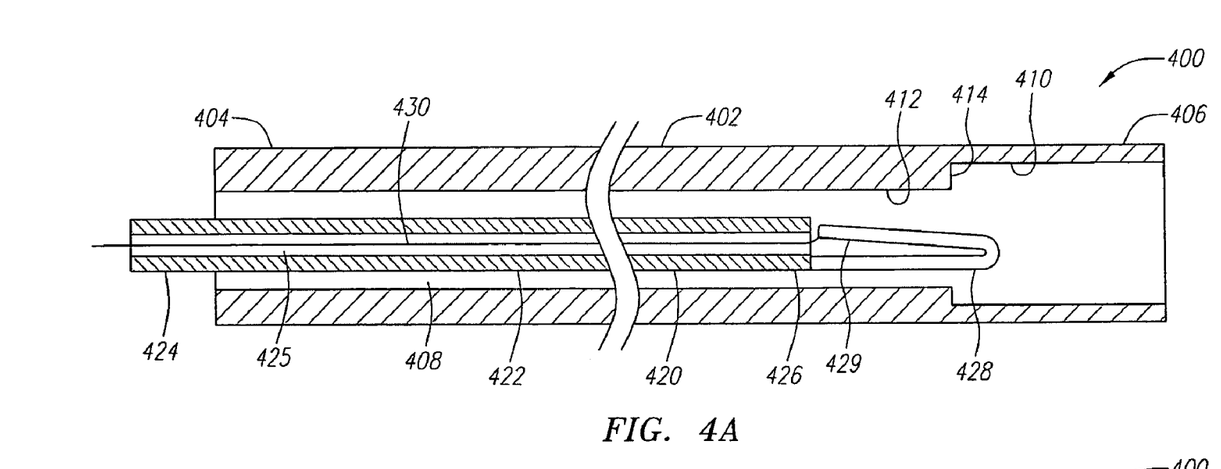
FIGS. 4A and 4B illustrate a catheter for providing access into a body in accordance with another embodiment of the invention, showing a variation of a steering device.
Figure 4B:
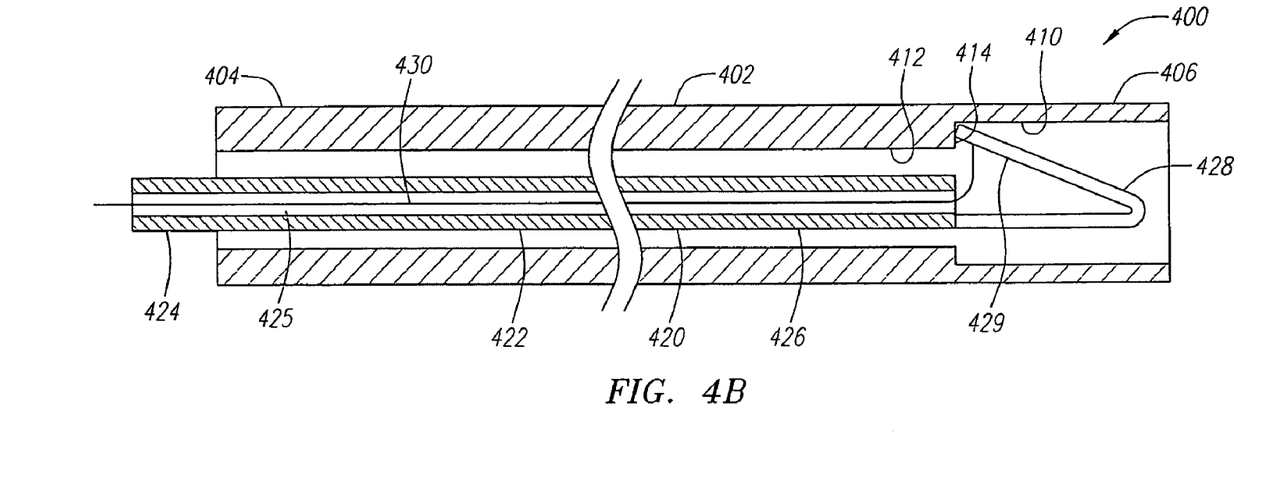

FIGS. 4A and 4B illustrates a catheter 400 in accordance with another embodiment of the invention. The catheter 400 includes a cannula 402 and a steering device 420. The cannula 402 has a proximal end 404, a distal end 406, and a lumen 408 extending therebetween. A wall 410 of the cannula 402 at the distal end 406 is relatively thinner than an adjacent wall 412, thereby creating a recess 414. The steering device 420 includes a shaft 422 having a proximal end 424, a distal end 426, and a lumen 425 extending therebetween, and an anchor member 428 secured to the distal end 426. The steering device 420 also includes a filament 430, such as a wire or a string, disposed within the lumen 425, and is secured to a portion 429 of the anchor member 428. The anchor member 428 can be bent into a low profile (FIG. 4A), and can assume an opened or expanded configuration when a bending force is removed or reduced. The anchor member 428 is made from an elastic material, such as nitinol, stainless steel, or a plastic. In the illustrated embodiment, the anchor member 428 is secured to the distal end 426 by a suitable adhesive. Alternatively, the anchor member 428 can be an extension of the shaft 422 that is fabricated together with the shaft 422 as a single unit.

During use, tension is applied to the filament 430 to bent the anchor member 428 into a low profile (FIG. 4A), and the steering device 420 is then inserted into the lumen 408 of the cannula 402. The anchor member 428 is advanced distally until it reaches the distal end 406. The tension in the filament 430 is then released to allow the anchor member 428 to assume an opened configuration, thereby anchoring the portion 429 against the recess 414 (FIG. 4B). Alternatively, instead of applying a tension force to the filament 430, the anchor member 428 can be inserted into the lumen 408 and allows an interior surface of the wall 412 to compress or bent the anchor member 428. In such case, the anchor member 428 is advanced distally until it passes the recess 414, at which point, the anchor member 428 will spring open and anchor itself against the recess 414. After the steering device 420 has been secured to the cannula 402, it can be used to steer the distal end 406 of the cannula 402 as similarly discussed previously. When it is desired to remove the steering device 420, tension force can be applied to the filament 430 to bent the anchor member 428 into a low profile to disengage the anchor member 428 from the recess 414. The steering device 420 can then be removed from the lumen 408 of the cannula 402.

Figure 5A:
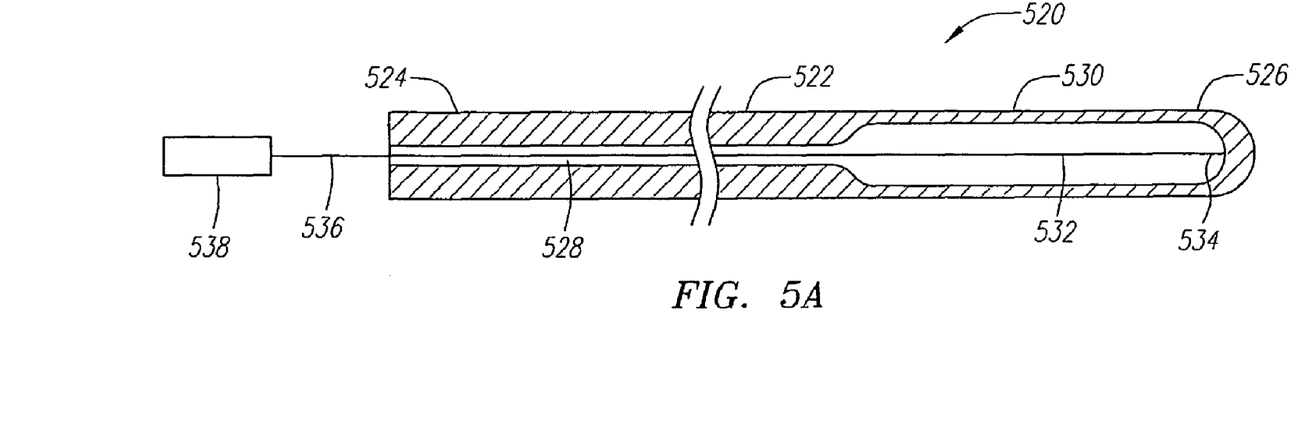
FIGS. 5A and 5B illustrate another variation of a steering device.
Figure 5B:
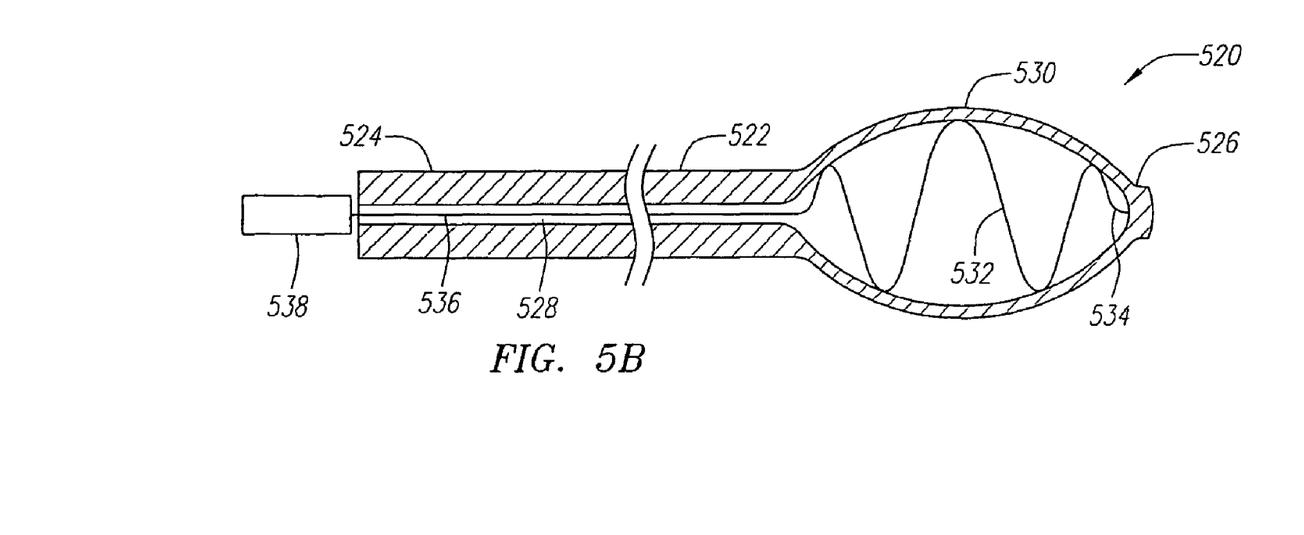

FIGS. 5A and 5B show another variation of a steering device 520 that can be used to detachably secure to a cannula to provide steering functionality to the cannula. The steering device 520 includes a shaft 522 having a proximal end 524, a distal end 526, and a lumen 528 extending therebetween. A wall 530 of the shaft 522 is relatively thinner than an adjacent wall. The steering device 520 also includes a wire 532 having a distal end 534 secured to the distal end 526 of the shaft 522, and a proximal end 536 secured to a handle 538. The wire 532 is made of an elastic material, such as nitinol, and has an expanded configuration (FIG. 5B). When using the device 520, tension force is applied to the wire 532 to stretch the wire 532 into a substantially linear profile (FIG. 5A). The device 520 is then inserted into a lumen of a cannula, and is advanced until the distal end 526 is desirably place. Next, the tension force in the wire 532 is reduced or removed (e.g., by releasing the handle 538), thereby allowing the wire 532 to assume the expanded configuration. The wire 532 pushes the wall 530 radially outward and compresses against an interior wall of the lumen of the cannula, thereby securing the device 520 to the cannula. The device 520 can then be used to steer a distal end of the cannula (e.g., by pulling the proximal end 524) as similarly discussed previously.

It should be noted that the manner in which the steering device is detachably secured to the cannula should not be limited to the examples discussed previously, and that a variety of securing mechanisms can be employed. For examples, in alternative embodiments, the steering device can include a screw, a snap-fit connector, a frictional type connector, or other securing mechanisms for detachably securing the steering device to the cannula. Also, in alternative embodiments, the steering device or the cannula can include a locking mechanism made from an elastic or supper elastic material (e.g., Nitinol or polymer(s)), thereby allowing the steering device to be detachably secured to the cannula by a changing shape of the locking mechanism.

Figure 6:
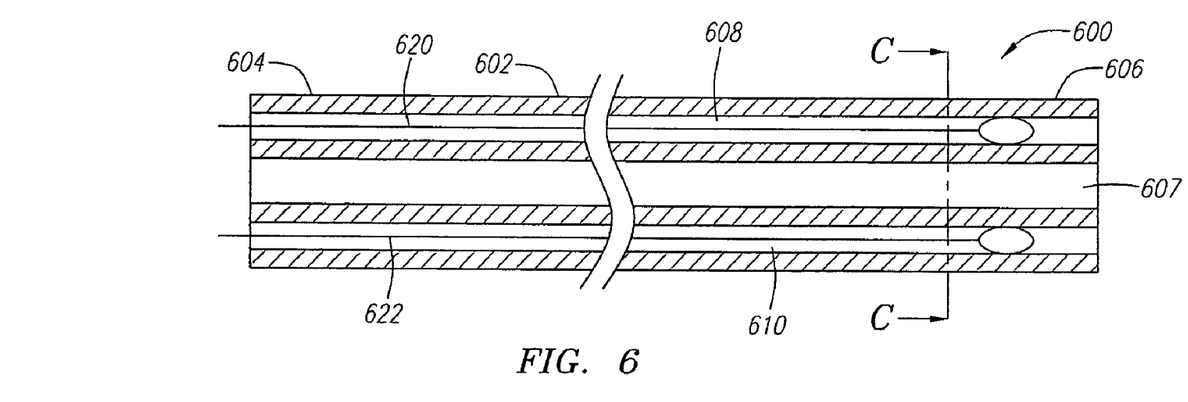
FIG. 6 illustrates a catheter for providing access into a body in accordance with other embodiments of the invention, showing the catheter having a plurality of steering devices.

In the previously described embodiments, the catheter includes one steering device. Alternatively, any of the embodiments of the catheter described previously can include one or more additional steering devices that can be inserted in one or more additional lumens of a cannula. In addition, any of the cannulas described previously can further include a working channel such that the steering device can remain secured to the cannula while the working channel is used to deliver objects or fluid. FIG. 6 shows a catheter 600 that includes a cannula 602, a first steering device 620, and a second steering device 622. The cannula 602 has a proximal end 604, a distal end 606, and a working channel 607, a first and a second lumens 608, 610 extending therebetween. The steering devices 620, 622 are similar to that described with reference to FIGS. 1A and 1B. The steering devices 620, 622 are configured to be inserted into the lumens 608, 610, respectively, and can be secured to the cannula 602, as similarly discussed previously. In the illustrated embodiment, the first and second lumens 608, 610 are spaced 1800 from each other. Such configuration allows a bi-directional steering of the distal end 606 of the cannula 602 in opposite directions by selectively applying tension to either the first steering device 620 or the second steering device 622. Alternatively, the first and second lumens 608, 610 can be spaced at other angles. Although only two steering devices 620, 622 are shown, in alternative embodiments, the catheter 600 can include more than two lumens for housing more than two steering devices 620, 622, thereby allowing steering of the distal end 606 in more than two directions.

During use, the steering devices 620, 622 are inserted into the lumens 608, 610 of the cannula 602, and are secured to the cannula 602. The distal end 606 of the cannula 602 is then inserted into a body and is steered by pulling either of the steering devices 620, 622. When the distal end 606 reaches a desired position, the first and the second steering devices 620, 622 can remain secured to the cannula 602, while the working channel 607 can be used to deliver an object or fluid. In an alternative embodiment, the cannula 602 does not include the working channel 607. In such case, after the distal end 606 has been desirably positioned within the body, one or both of the steering devices 620, 622 can be removed from the lumens, 608, 610, respectively, and the unoccupied lumen(s) can be used to deliver an object or fluid, as similarly described previously.

Figure 7A:
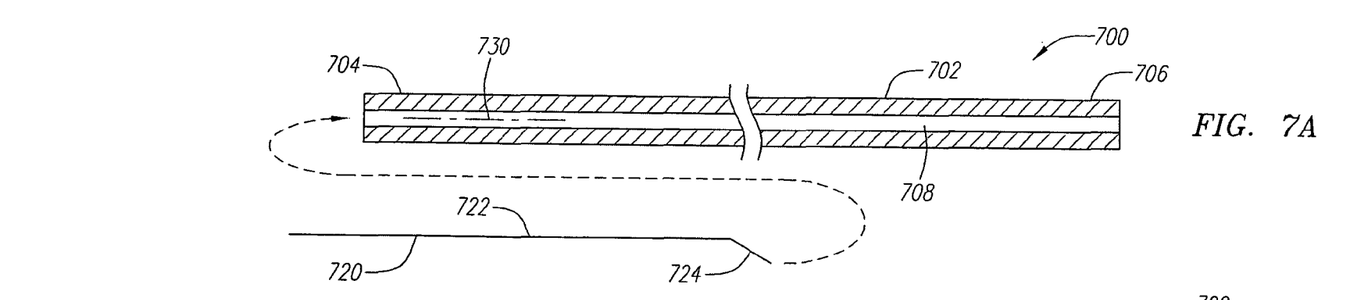
FIG. 7A illustrates a catheter for providing access into a body in accordance with another embodiment of the invention, which includes a working channel for housing a slidable steering wire.
Figure 7B:
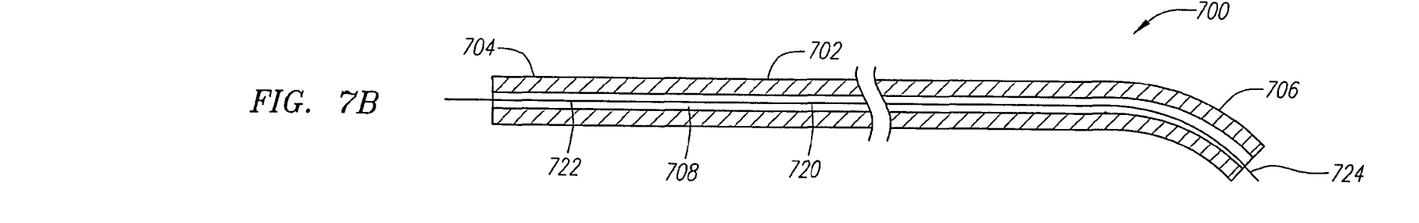
FIG. 7B illustrates the catheter of FIG. 7A, showing a distal end of a cannula being steered as the steering wire is advanced distally.

Although the steering devices have been described as being detachably secured to a cannula such that the steering device does not slide relative to the cannula, the scope of the invention should not be so limited. FIGS. 7A and 7B illustrate a catheter 700 in accordance with another embodiment of the invention. The catheter 700 includes a cannula 702 and a steering device 720 that is configured to be slidable relative to the cannula 702 for steering the cannula 702. The cannula 702 has a proximal end 704, a distal end 706, and a lumen 708 extending therebetween. The steering device 720 includes a wire 722 having a bent distal end 724.

During use, the wire 722 is at least partially inserted into the lumen 708 of the cannula 702, and the cannula 702 is inserted into a body. The distal end 706 can be steered by sliding the distal end 724 of the wire 722 either distally or proximally relative to the cannula 702. Particularly, when the bent distal end 724 is confined within the lumen 708 and is located away from the distal end 706 of the cannula 702, the distal end 724 is stretched or compressed into a low profile. When the bent distal end 724 is placed adjacent the distal end 706 of the cannula 702, the stiffness of the bent distal end 724 predominates the stiffness of the distal end 706 of the cannula 702, thereby causing the cannula 702 to bend in a direction of the bent distal end 724 (FIG. 7B). When it is desirable to steer the distal end 706 in a different direction, the wire 722 can be retrieved proximally, rotated about an axis 730 such that the bent distal end 724 is oriented in a different radial direction, and re-inserted into the lumen 708. In an alternative embodiment, the distal end 706 of the cannula 702 can be made relatively more flexible than a proximal portion of the cannula 702 (e.g., by constructing a distal portion of the cannula 702 using a material that is more flexible that that for a proximal portion) to thereby allow ease of bending at the distal end 706.

Figure 8:
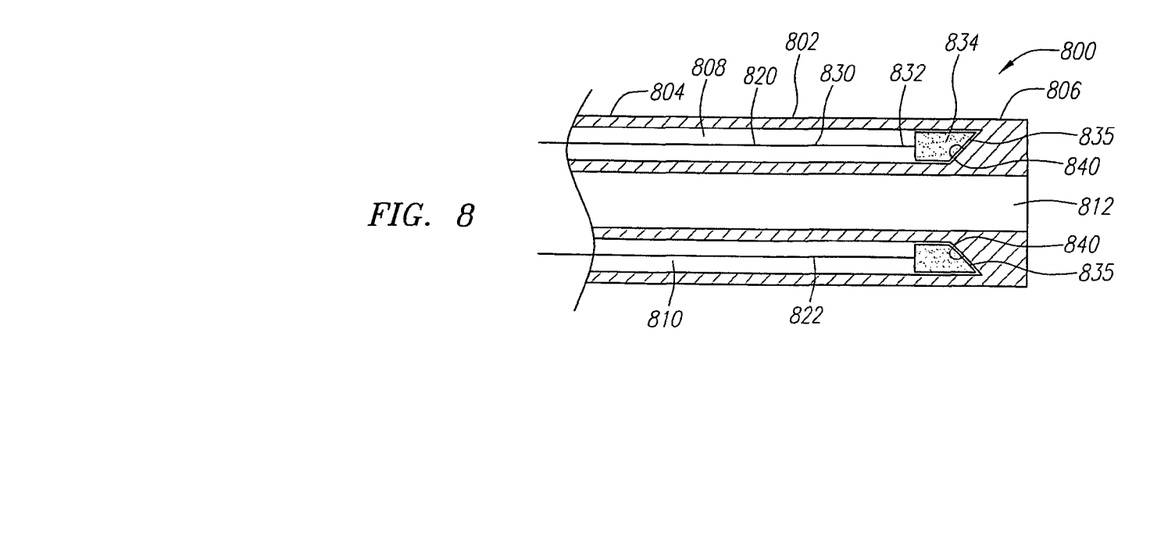
FIG. 8 illustrates a catheter for providing access into a body in accordance with another embodiment of the invention, showing the catheter having a plurality of stiffening elements engaging with a cannula.

It should be noted that besides providing steering functionality to a cannula, any of the steering devices described previously can also be used as a stiffening element to increase a stiffness (e.g., bending stiffness, axial stiffness, and torsional stiffness) of a cannula. In this sense, the device (e.g., device 120, 220, 320, 420, 520, 620, 622, or 720) functions as a reinforcing when placed within a lumen of a cannula. It should be noted that when any of these devices is being used as a stiffening element, the device can be secured or unsecured to the cannula. FIG. 8 shows a catheter 800 having a cannula 802, a first stiffening element 820, and a second stiffening element 822. The cannula 802 has a proximal end 804, a distal end 806, and a first and a second lumens 808, 810 and a working channel 812 extending therebetween. The working channel 812 can be used to deliver a tool, an instrument, a therapeutic element, a diagnostic element, or fluid, as similarly discussed previously. The stiffening elements 820, 822 each includes an elongate member 830 (e.g., a wire, a fiber, a coil, or other structures that can function as reinforcing) having a distal end 832, and a coupling device 834 secured to the distal end 832. The coupling device 834 has a slanted planar surface 835 that is configured to mate with a slanted surface 840 located within each of the lumens 808, 810. Such configuration improves a torsional stiffness of the cannula 802, and allows a higher level of torsional (or torqueing) force be transmitted from the proximal end 804 to the distal end 806.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, instead of securing a steering/stiffening device to a distal end of a cannula, the steering/stiffening device can be secured to the cannula at other locations along its length. In addition, instead of having only one securing mechanism, in alternative embodiments, any of the steering/stiffening devices described previously can have a plurality of securing mechanisms located along its length, thereby allowing the steering/stiffening device to be secured to the cannula at multiple locations along a length of the cannula. Furthermore, in alternative embodiments, any of the cannulas described previously can further include additional lumen(s) or channel(s) for housing fiber optics, which can be used to deliver light energy to a distal end of the cannula, and/or collect image signals at the distal end of the cannula.

The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. An apparatus for accessing a site within a body, comprising:
    a cannula having a proximal end, a distal end, and a lumen extending there between and a central longitudinal axis;
    a steering mechanism comprising a flexible elongate member having a distal end sized for insertion through the cannula lumen and configured to move, in situ, from a configuration where the steering mechanism is detached from the cannula to a configuration wherein the steering mechanism is attached to the cannula; and
    a handle secured to a proximal end of the elongate member, the handle having a tensioning device for applying a tension to the elongate member,
    wherein the steering mechanism is proximal the distal end of the cannula when the steering mechanism is attached to the cannula, and
    wherein the distal end of the steering mechanism has a shape that is radially asymmetrical with respect to the central longitudinal axis of the cannula when the steering mechanism is attached to the cannula,
    wherein the distal end of the elongate member has an expanded configuration and a collapsed configuration, wherein the elongate member may be secured to the distal end of the cannula when the elongate member distal end is in the expanded configuration, and
    wherein the distal end of the elongate member comprises a bent wire.

2. The apparatus of claim 1, wherein the cannula further includes a working channel extending between its distal and proximal ends, the working channel having a cross sectional dimension sized to house an object selected from the group consisting of at least a portion of a guidewire, at least a portion of an ablation device, at least a portion of an imaging device, at least a portion of a fiber optic, a therapeutic element, a diagnostic element, and an implant.

* * * * *